US012590922B2

(12) United States Patent (10) Patent No.: US 12,590,922 B2
Watanabe et al. (45) Date of Patent: Mar. 31, 2026

(54) GAS SENSOR AND CONCENTRATION CORRECTION METHOD FOR USE IN GAS SENSOR

(71) Applicant: NGK INSULATORS, LTD., Nagoya (JP)

(72) Inventors: Yusuke Watanabe, Nagoya (JP); Taku Okamoto, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 360 days.

(21) Appl. No.: 18/159,830

(22) Filed: Jan. 26, 2023

(65) Prior Publication Data

US 2023/0324327 A1 Oct. 12, 2023

(30) Foreign Application Priority Data

Mar. 18, 2022 (JP) ................................. 2022-043681

(51) Int. Cl.
*G01N 27/406* (2006.01)
*G01N 27/407* (2006.01)
(Continued)

(52) U.S. Cl.
CPC ..... *G01N 27/4065* (2013.01); *G01N 27/4078* (2013.01); *G01N 27/41* (2013.01); *G01N 33/0037* (2013.01)

(58) Field of Classification Search
CPC .......... G01N 27/4065; G01N 27/4078; G01N 27/41; G01N 33/0037
See application file for complete search history.

(56) References Cited

U.S. PATENT DOCUMENTS 6,082,176 A * 7/2000 Kondo ............... G01N 33/0037
73/23.31
9,494,548 B2 11/2016 Furuta
(Continued)

FOREIGN PATENT DOCUMENTS

CN 110274946 A 9/2019
JP 5832479 B2 12/2015
(Continued)

OTHER PUBLICATIONS

Chinese Office Action received in corresponding Chinese Application No. 202310011127.2 dated Sep. 20, 2025.

*Primary Examiner* — James Lin
*Assistant Examiner* — Vivian A Tran
(74) *Attorney, Agent, or Firm* — MATTINGLY & MALUR, PC

(57) ABSTRACT

A controller of a gas sensor includes: a concentration identification part identifying a concentration of a predetermined gas component based on a measurement pump current flowing between a measurement electrode and an out-of-space pump electrode in accordance with the concentration of the predetermined gas component due to application of a predetermined pump voltage; and a correction processing part correcting the concentration of the predetermined gas component identified by the concentration identification part, the correction processing part corrects the concentration of the predetermined gas component based on a correlation identified in advance between an offset current value as a magnitude of the measurement pump current when a measurement gas not containing the predetermined gas component flows or a normalized value of the offset current value and output fluctuations of the measurement pump current at startup of the gas sensor.

2 Claims, 8 Drawing Sheets

(51) Int. Cl.
  _G01N 27/41_      (2006.01)
  _G01N 33/00_      (2006.01)

(56)              References Cited

U.S. PATENT DOCUMENTS

| | | | |
|---|---|---|---|
| 9,494,584 B2 | 11/2016 | Lee et al. | |
| 9,804,118 B2 | 10/2017 | Sekiya et al. | |
| 2015/0276659 A1* | 10/2015 | Sekiya | G01N 27/4071 |
| | | | 204/416 |
| 2019/0285573 A1 | 9/2019 | Watanabe et al. | |
| 2021/0364465 A1* | 11/2021 | Azuma | G01N 27/41 |
| 2022/0074888 A1* | 3/2022 | Hagino | G01N 33/0009 |
| 2024/0302321 A1* | 9/2024 | Tanaka | G01N 27/26 |

FOREIGN PATENT DOCUMENTS

| | | | |
|---|---|---|---|
| JP | 6401644 B2 | 10/2018 | |
| JP | 2020-71128 A | 5/2020 | |

* cited by examiner

F I G . 1
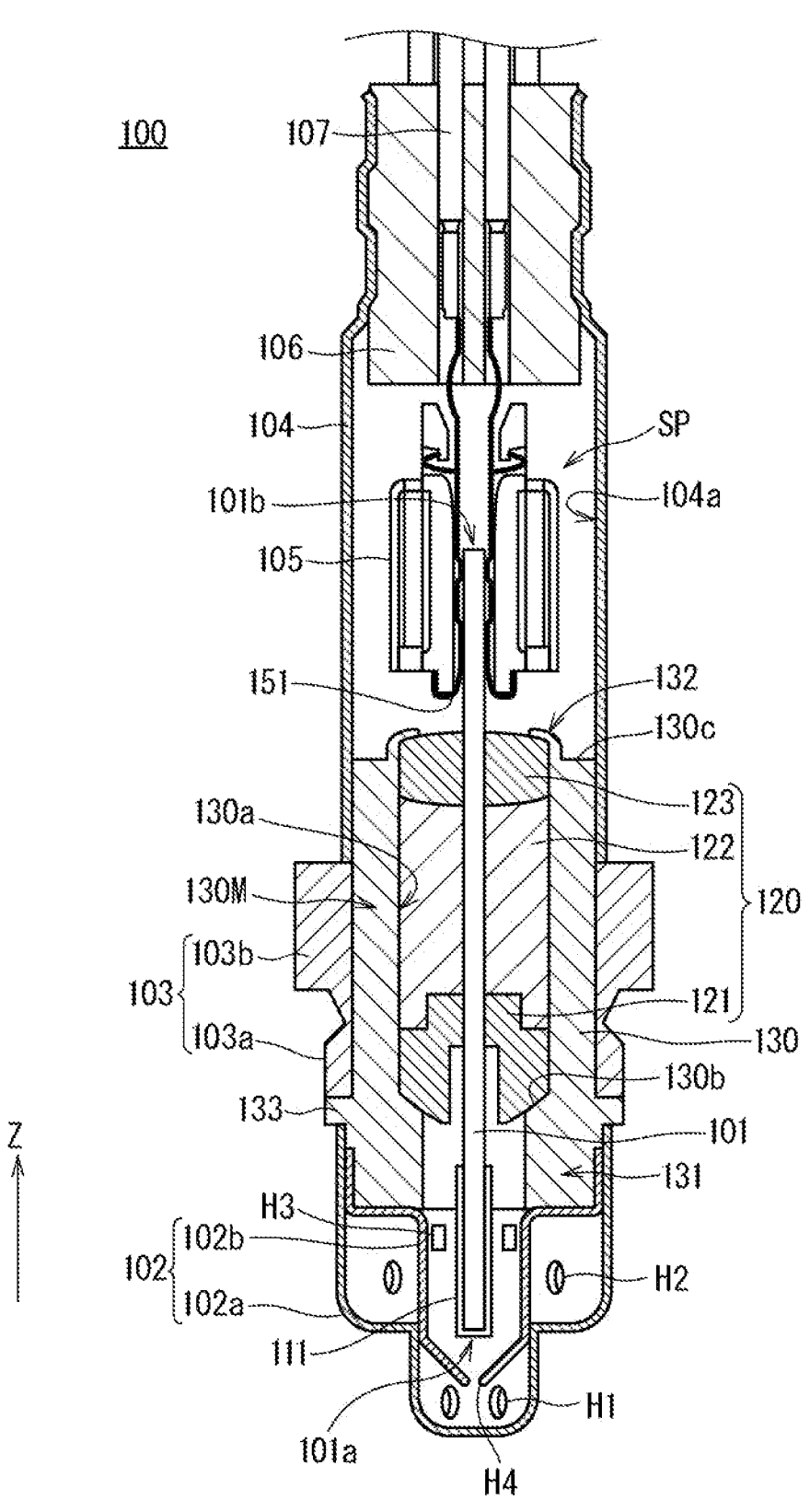

GAS SENSOR AND CONCENTRATION CORRECTION METHOD FOR USE IN GAS SENSOR

CROSS-REFERENCE TO RELATED APPLICATION

The present application claims priority from Japanese application JP2022-043681, filed on Mar. 18, 2022, the contents of which is hereby incorporated by reference into this application.

BACKGROUND OF THE INVENTION

Field of the Invention

The present invention relates to a gas sensor including a sensor element of ceramics, and, in particular, to securement of measurement accuracy of the gas sensor.

Description of the Background Art

As a device for measuring a concentration of a predetermined gas component in a measurement gas, such as a combustion gas and an exhaust gas from an internal combustion engine typified by an engine of a vehicle, a gas sensor including a sensor element formed of oxygen-ion conductive solid electrolyte ceramics, such as zirconia ($ZrO_2$), has conventionally been known.

The gas sensor typically includes a main body having a configuration in which an elongated planar sensor element (detection element) of ceramics is secured in (a hollow portion of) a containment member of metal by a ceramic supporter and a powder compact of ceramics, such as talc, and the powder compact hermetically seals a portion between a side of one end portion where a gas inlet for introducing the measurement gas to an inside of the element where a measurement electrode and the like are arranged is provided and a side of the other end portion where a reference gas (air) is introduced (see Japanese Patent No. 6401644, for example).

A portion of the containment member on a side of the other end portion is a cylindrical member also referred to as a so-called outer tube, and a rubber plug is fit into a leading end thereof as a seal (sealing) member. A space surrounded by the outer tube and the rubber plug is a reference gas space. The rubber plug has through holes into which some lead lines electrically connecting the sensor element and an outside are inserted. Air present in the outer tube when the rubber plug is fit into the outer tube in a process of manufacturing the gas sensor is typically used as the reference gas, but air entering into the outer tube through gaps between the through holes of the rubber plug and the lead lines thereafter can also be the reference gas.

In the other end portion of the sensor element, the reference gas is introduced from the reference gas space into the element, and a reference electrode providing a reference potential is disposed to be contactable with the reference gas. The reference electrode is to be in contact with the reference gas having a constant oxygen concentration, so that the reference potential is maintained constant to cause a potential difference between the reference electrode and another electrode, such as the measurement electrode, of the sensor element in accordance with an atmosphere around the electrode.

While various electrodes of the sensor element are electrically connected to connection terminals in the end portion of the element by electrode leads arranged in or on a side of the element, a sensor element including a porous reference electrode lead connecting the reference electrode and an electrode pad as one of the connection terminals has also already been known (see Japanese Patent No. 5832479, for example).

In addition, a gas sensor element in which a width W1 of a measurement gas chamber into which a measurement gas is introduced and a width W2 of a porous diffusion resistance layer disposed at a gas inlet to the measurement gas chamber satisfy a relationship W1<W2 has already been known (see Japanese Patent Application Laid-Open No. 2020-71128, for example).

A gas sensor as disclosed in Japanese Patent No. 6401644 is used under an exhaust gas atmosphere with the main body thereof being disposed along an exhaust path from the engine, and is used under a high temperature environment with the sensor element itself being heated by a heater. Thus, when the main body is heated to a high temperature upon start of use, a contaminated gas generated due to volatilization of an oil content adhering to an inner surface of the outer tube and generation of a gas from the rubber plug might contaminate the reference gas. As a result of the contaminated gas reaching the reference electrode, the reference potential to be maintained constant might change, thereby to fail to maintain measurement accuracy of the gas sensor. Such a situation is more likely to arise when the reference electrode lead is porous as disclosed in Japanese Patent No. 5832479.

In the gas sensor disclosed in Japanese Patent No. 6401644, an electrochemical pump cell including an outer electrode, the reference electrode, and a solid electrolyte disposed between the electrodes can pump in oxygen from outside the element to the reference gas space by applying a predetermined voltage across the electrodes, and, through pumping in, the reference potential can be maintained constant even when the reference gas is contaminated.

The above-mentioned contaminated gas, however, sometimes not only reach the reference electrode but also reach the measurement electrode and, further, an internal space closer to the gas inlet via an electrode lead, such as a measurement electrode lead. The measurement gas to reach the measurement electrode with an oxygen concentration being adjusted at a predetermined value after being introduced through the gas inlet might be contaminated by the contaminated gas entering through the lead, and, as a result, measurement accuracy of the gas sensor might be deteriorated. Even if the amount of the entering contaminated gas is minute, an effect thereof is not negligible when a gas component to be measured has a low concentration.

For example, Japanese Patent Application Laid-Open No. 2020-71128 discloses that, in the case that the width W1 of the measurement gas chamber is smaller than a conventional width, and thus the electrode of the gas sensor element has a smaller width, the electrode lead connected to each electrode is set to have a relatively large width so that an electrode portion including a lead portion is adjusted to have predetermined electrode impedance, in order not to cause a great change in impedance. When a width of the lead portion is increased as described above, diffusion resistance of the lead portion might be reduced to increase the amount of the contaminated gas reaching via the lead portion.

Use of the porous electrode lead as disclosed in Japanese Patent No. 5832479 for a lead other than the reference electrode lead can suppress the amount of platinum to be used and lead to reduction in cost, but might increase the amount of the contaminated gas entering through the electrode lead.

SUMMARY

The present invention is directed to a gas sensor including a sensor element of ceramics, and, in particular, relates to securement of measurement accuracy of the gas sensor.

According to the present invention, a gas sensor capable of sensing a predetermined gas component in a measurement gas includes: a sensor element including an elongated planar base part formed of an oxygen-ion conductive solid electrolyte, and including a sensing part on a side of one end portion thereof; a casing in which the sensor element is contained and secured; and a controller controlling operation of the gas sensor. The casing includes: an outer tube having a reference gas space in which a reference gas is present and into which the other end portion of the sensor element protrudes; and a seal member fit into an end portion of the outer tube to seal the reference gas space. The sensor element includes: at least one oxygen partial pressure adjustment internal space communicating with an inlet for the measurement gas disposed on a side of the one end portion under predetermined diffusion resistance; a measurement internal space further communicating with the at least one oxygen partial pressure adjustment internal space; an out-of-space pump electrode disposed at a location other than the at least one oxygen partial pressure adjustment internal space and the measurement internal space; a measurement electrode disposed to face the measurement internal space; a measurement pump cell to which a predetermined pump voltage is applied to allow a measurement pump current to flow between the measurement electrode and the out-of-space pump electrode in accordance with a concentration of the predetermined gas component; and a measurement electrode lead portion including a measurement electrode lead and a measurement lead insulating layer, the measurement electrode lead extending from the measurement electrode to electrically connect an outside of the sensor element and the measurement electrode, the measurement lead insulating layer covering the measurement electrode lead. The controller includes: a concentration identification element configured to identify the concentration of the predetermined gas component based on the measurement pump current; and a correction processing element configured to correct the concentration of the predetermined gas component identified by the concentration identification element. The correction processing element corrects the concentration of the predetermined gas component based on a correlation identified in advance between an offset current value or a normalized value of the offset current value and output fluctuations of the measurement pump current at startup of the gas sensor. The offset current value is a magnitude of the measurement pump current when a measurement gas not containing the predetermined gas component flows.

According to the present invention, deterioration of measurement accuracy of a NOx concentration caused by generation of a contaminated gas in the reference gas space at activation of the gas sensor can be suppressed.

It is thus an object of the present invention to provide a gas sensor enabling suppression of deterioration of measurement accuracy even when a contaminated gas is generated on a side of a reference gas space.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a partial cross-sectional view along a longitudinal direction of a gas sensor 100;

FIG. 4 is a plan view illustrating the layout of electrode lead portions including electrode leads extending from an inner pump electrode 22, an auxiliary pump electrode 51, and a measurement electrode 44;

FIG. 8 describes how to evaluate the amount of output fluctuations; and

DESCRIPTION OF THE PREFERRED EMBODIMENTS

<Configuration of Gas Sensor>

Figure 2:
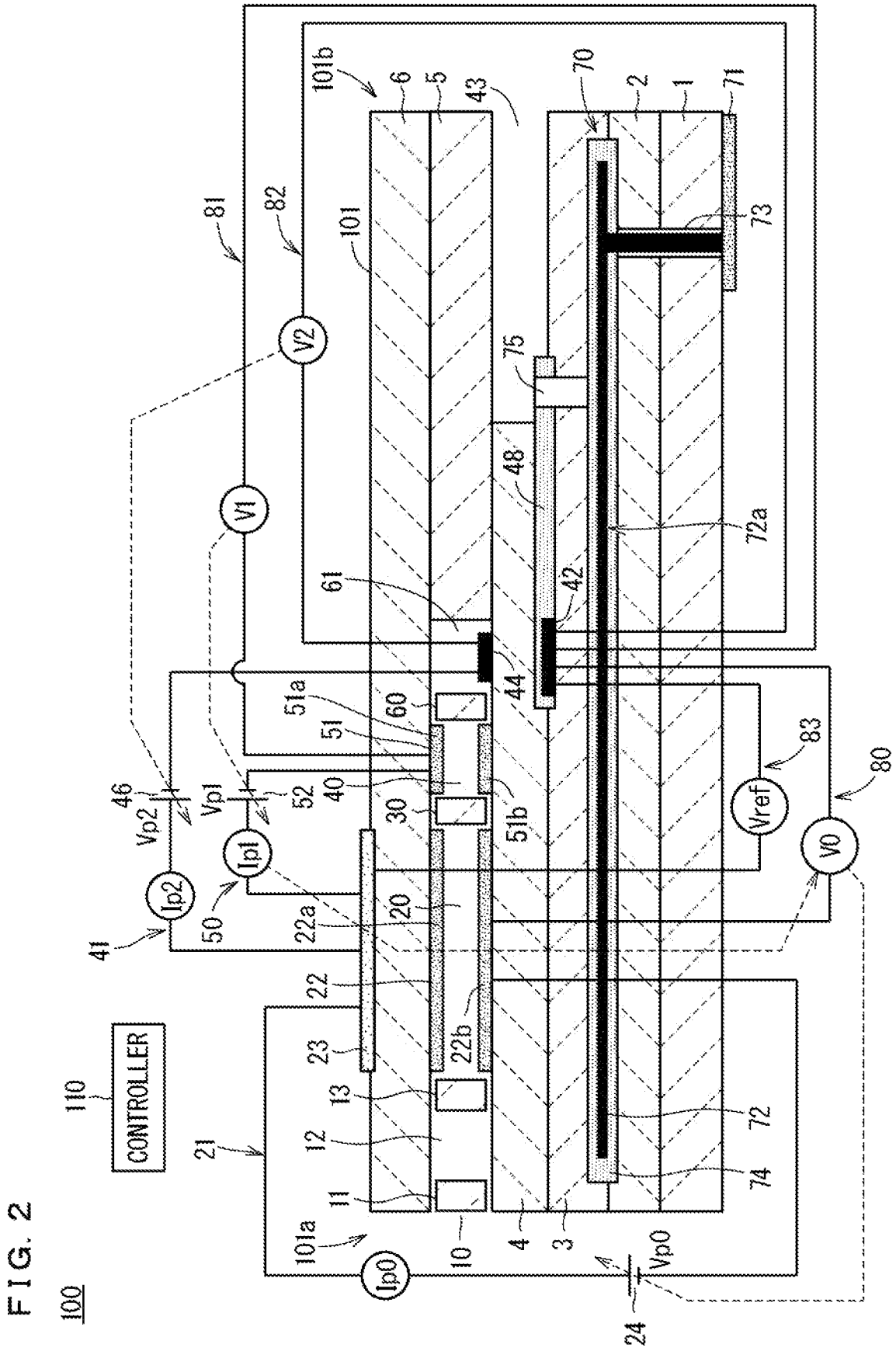
FIG. 2 is a vertical cross-sectional view along a longitudinal direction of a sensor element 101 schematically showing one example of a configuration of the sensor element 101.

FIG. 1 is a partial cross-sectional view along a longitudinal direction of (more particularly a main body of) a gas sensor 100 according to an embodiment of the present invention. In the present embodiment, the gas sensor 100 is used by being attached to an exhaust path of an unillustrated internal combustion engine (e.g., an engine of a vehicle), and detects, using a sensor element 101 disposed therein, a predetermined gas component (e.g., NOx) contained in an exhaust gas as a measurement gas flowing through the exhaust path. In FIG. 1, a vertical direction is shown as a z-axis direction, and the longitudinal direction of the gas sensor 100 matches the z-axis direction (the same applies to subsequent drawings).

A case where the internal combustion engine is the engine of the vehicle, and the gas component to be detected by the gas sensor 100 is NOx will be described below. A scheme of identifying a NOx concentration and correcting the identified NOx concentration described in the present embodiment, however, is applicable to the other types of gases allowing for measurement and correction based on a similar principle.

The gas sensor 100 mainly has a configuration in which the sensor element 101, an annularly-mounted component 120 annularly mounted to the sensor element 101, and a tubular body 130 further annularly mounted around the annularly-mounted component 120 to contain the annularly-mounted component 120 are covered with a protective cover 102, a fixing bolt 103, and an outer tube 104. In other words, the gas sensor 100 generally has a configuration in which the sensor element 101 penetrates the tubular body 130 in an axial direction at a location of an axial center in the tubular body 130, and the annularly-mounted component 120 is annularly mounted around the sensor element 101 in the tubular body 130. The tubular body 130, the protective cover 102, and the outer tube 104 mainly constitute a casing (containment member) for the sensor element 101.

The sensor element 101 is an elongated columnar or laminar member including an element body formed of oxygen-ion conductive solid electrolyte ceramics, such as zirconia, as a main constituent material. The sensor element 101 is disposed on a central axis along a longitudinal direction of the tubular body 130. A direction of extension of the central axis matching the longitudinal direction of the tubular body 130 is hereinafter also referred to as an axial direction. In FIG. 1 and subsequent drawings, the axial direction matches the z-axis direction.

The sensor element 101 has a configuration in which a sensing part including a gas inlet, internal spaces, and the like is located on a side of a first leading end portion 101a, and various electrodes and wiring patterns are located on a surface of and in the element body. In the sensor element 101, a test gas introduced into the internal spaces is reduced or decomposed in the internal spaces to generate oxygen ions. Based on proportionality between a quantity of oxygen ions flowing through the element and a concentration of the gas component in the test gas, the gas sensor 100 determines the concentration of the gas component.

A portion on a surface of the sensor element 101 in a predetermined range from the first leading end portion 101a along the longitudinal direction is covered with a protective film 111. The protective film 111 is disposed to protect a portion in the vicinity of the first leading end portion 101a of the sensor element 101 where the internal spaces, the electrodes, and the like are provided, from thermal shock caused by wetting and the like, and is also referred to as a thermal shock resistant protective layer. The protective film 111 is a porous film formed, for example, of $Al_2O_3$ and having a thickness of approximately 10 μm to 2000 μm. The protective film 111 is preferably formed to be able to withstand force of up to approximately 50 N in light of the purpose thereof. A range of formation of the protective film 111 in FIG. 1 and subsequent drawings is just an example, and an actual range of formation is determined as appropriate in accordance with a specific structure of the sensor element 101.

The protective cover 102 is a substantially cylindrical exterior member for protecting the first leading end portion 101a as a portion of the sensor element 101 to be in direct contact with the test gas during use. The protective cover 102 is fixed to an outer peripheral end portion (an outer periphery of a reduced diameter portion 131 described below) on a lower side in FIG. 1 (a negative side in the z-axis direction) of the tubular body 130 by welding.

In a case illustrated in FIG. 1, the protective cover 102 has a two-layer structure of an outer cover 102a and an inner cover 102b. The outer cover 102a and the inner cover 102b respectively have a plurality of through holes H1 and H2 and a plurality of through holes H3 and H4 that allow a gas to pass. The types, the numbers, the locations, the shapes, and the like of the through holes illustrated in FIG. 1 are just examples, and may be determined as appropriate in view of an in-flow manner of the measurement gas into the protective cover 102.

The fixing bolt 103 is an annular member used when the gas sensor 100 is fixed to a measurement location. The fixing bolt 103 includes a threaded bolt portion 103a and a holding portion 103b to be held when the bolt portion 103a is screwed. The bolt portion 103a is to be screwed with a nut disposed at an attachment location of the gas sensor 100. For example, the bolt portion 103a is screwed with a nut portion provided on an exhaust pipe of the vehicle, so that the gas sensor 100 is fixed to the exhaust pipe with a side of the protective cover 102 thereof being exposed in the exhaust pipe.

The outer tube 104 is a cylindrical member of metal having one end portion (a lower end portion in FIG. 1) fixed to an outer peripheral end portion on an upper side in FIG. 1 (a positive side in the z-axis direction) of the tubular body 130 by welding. A connector 105 is disposed in the outer tube 104. A rubber plug 106 is fit into the other end portion (an upper end portion in FIG. 1) of the outer tube 104 as a seal (sealing) member. In the gas sensor 100, a space surrounded by the outer tube 104 between the tubular body 130 and the rubber plug 106 is a reference gas space SP. In other words, the reference gas space SP is sealed by the rubber plug 106. A second leading end portion 101b of the sensor element 101 protrudes into the reference gas space SP. Air is introduced into the reference gas space SP as a reference gas when the NOx concentration is measured, for example.

The connector 105 includes a plurality of contact members 151 being in contact with a plurality of unillustrated terminal electrodes located in the second leading end portion 101b of the sensor element 101. The contact members 151 are connected to lead lines 107 inserted into the rubber plug 106. The lead lines 107 are connected to a controller 110 and various power supplies, which are not illustrated in FIG. 1, outside the gas sensor 100.

Although only two contact members 151 and two lead lines 107 are illustrated in FIG. 1, they are just examples.

The tubular body 130 is a tubular member of metal also referred to as a main metal fitting. The sensor element 101 and the annularly-mounted component 120 are contained in the tubular body 130. In other words, the tubular body 130 is further annularly mounted around the annularly-mounted component 120, which is annularly mounted around the sensor element 101.

The tubular body 130 mainly includes a thick main portion 130M having a cylindrical inner surface 130a parallel to the axial direction, which forms a cylindrical internal space, the reduced diameter portion 131 disposed in a lower end portion in the axial direction in FIG. 1 (on the negative side in the z-axis direction) and being thicker than the main portion 130M, a thin swaged portion 132 extending further upward from an end surface 130c of the main portion 130M located at an upper end in the axial direction in FIG. 1 and bent toward the axial center, and a locking portion 133 protruding circumferentially outward.

With the swaged portion 132 being bent, the internally disposed annularly-mounted component 120 (directly, a second ceramic supporter 123) is pressed and fixed (constrained) from the upper side in FIG. 1. The swaged portion 132 is bent after annular mounting of the annularly-mounted component 120 to the sensor element 101 as will be described below.

The annularly-mounted component 120 includes a first ceramic supporter 121, a powder compact 122, and the second ceramic supporter 123.

The first ceramic supporter 121 and the second ceramic supporter 123 are each an insulator of ceramics. More particularly, the first ceramic supporter 121 and the second ceramic supporter 123 each have a rectangular through hole (not illustrated) in accordance with a cross-sectional shape of the sensor element 101 at a location of the axial center, and the sensor element 101 is inserted into the through hole, thereby to have the first ceramic supporter 121 and the second ceramic supporter 123 annularly mounted around the sensor element 101. The first ceramic supporter 121 is locked onto a tapered surface 130b of the tubular body 130 in a lower portion in FIG. 1.

On the other hand, the powder compact 122 is formed by molding powder of ceramics, such as talc, is disposed in the tubular body 130 in a state of being annularly mounted around the sensor element 101 with the insertion of the sensor element 101 into the through hole similarly to the first ceramic supporter 121 and the second ceramic supporter 123, and is then compressed for integration. More particularly, ceramic particles constituting the powder compact 122 are densely filled in a space enclosed by the first ceramic supporter 121, the second ceramic supporter 123, and the tubular body 130, through which the sensor element 101 penetrates.

In the gas sensor 100, generally, fixing of the sensor element 101 and the annularly-mounted component 120 in the tubular body 130 is implemented by locking the first ceramic supporter 121 onto the tapered surface 130b and pressing the second ceramic supporter 123 by the swaged portion 132 from above in FIG. 1. In addition, due to compression filling with the powder compact 122, airtight sealing between a side of the first leading end portion 101a and a side of the second leading end portion 101b of the sensor element 101 is implemented.

<General Configuration of Sensor Element and Controller>

FIG. 2 is a vertical cross-sectional view along the longitudinal direction of the element schematically showing one example of a configuration of the sensor element 101. FIG. 2 additionally shows the controller 110 controlling operation of each part of the gas sensor 100 and identifying the NOx concentration based on a NOx current (measurement pump current) flowing through the sensor element 101 while omitting illustration of the protective film 111 disposed on a side of the first leading end portion 101a of the sensor element 101.

The controller 110 includes at least one processor (not illustrated) and memory (not illustrated), and each of functions of the controller 110 is achieved by the processor executing software stored in the memory. The memory is nonvolatile or volatile semiconductor memory, for example.

Figure 3:
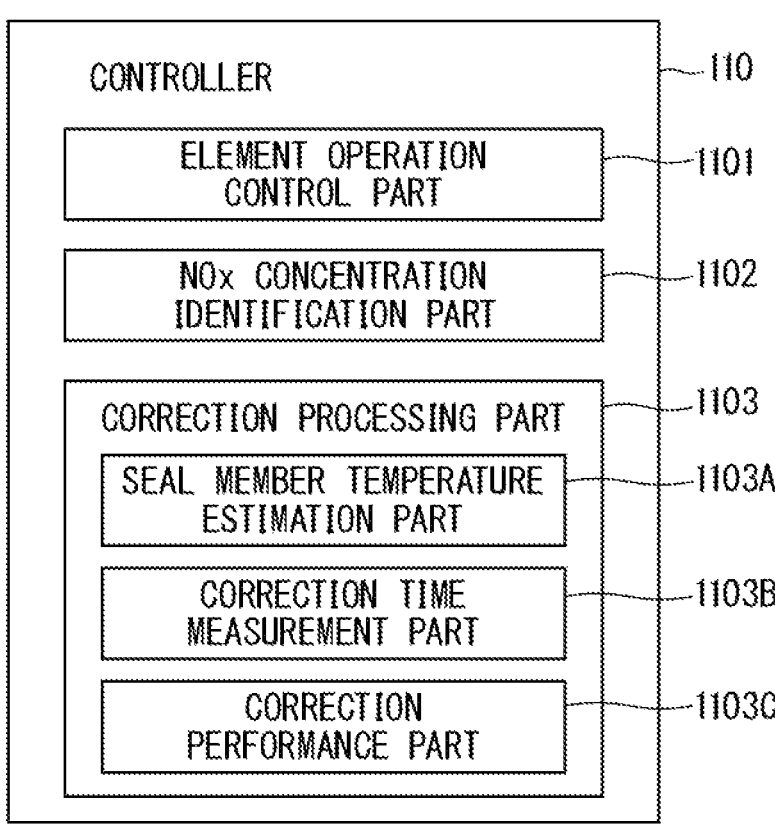
FIG. 3 is a block diagram showing functional components achieved by a controller 110.

FIG. 3 is a block diagram showing functional components achieved by the controller 110. The controller 110 includes, as the functional components, an element operation control part 1101 controlling operation of each part of the sensor element 101, a NOx concentration identification part 1102 identifying the NOx concentration, and a correction processing part 1103 correcting the NOx concentration identified by the NOx concentration identification part 1102 in a predetermined situation described below. The correction processing part 1103 includes a seal member temperature (rubber plug temperature) estimation part 1103A performing processing of estimating a temperature of the rubber plug 106, a correction time measurement part 1103B performing processing of measuring a time during which correction processing is performed and holding an accumulated value thereof (accumulated correction time), and a correction performance part 1103C actually performing correction processing.

Assume that the controller 110 includes an electronic control unit (ECU) (not illustrated) to which the gas sensor 100 is electrically connected and which controls operation of each part of the vehicle in the present embodiment.

The sensor element 101 is a planar (an elongated planar) element body of ceramics having a structure in which six solid electrolyte layers, namely, a first substrate layer 1, a second substrate layer 2, a third substrate layer 3, a first solid electrolyte layer 4, a spacer layer 5, and a second solid electrolyte layer 6 each formed of zirconia ($ZrO_2$) (e.g., yttria stabilized zirconia (YSZ)) as an oxygen-ion conductive solid electrolyte are laminated in the stated order from a lower side in FIG. 2. The solid electrolyte forming these six layers is dense and airtight. A surface on an upper side and a surface on a lower side of each of these six layers in FIG. 2 are hereinafter also simply referred to as an upper surface and a lower surface, respectively. A part of the sensor element 101 formed of the solid electrolyte as a whole is generically referred to as a base part.

The sensor element 101 is manufactured, for example, by performing predetermined processing, printing of circuit patterns (e.g., electrodes, electrode leads, and lead insulating layers), and the like on ceramic green sheets corresponding to the respective layers, then laminating them, and further firing them for integration.

Between a lower surface of the second solid electrolyte layer 6 and an upper surface of the first solid electrolyte layer 4 on a side of the first leading end portion 101a of the sensor element 101, a first diffusion control part 11 doubling as a gas inlet 10, a buffer space 12, a second diffusion control part 13, a first internal space 20, a third diffusion control part 30, a second internal space 40, a fourth diffusion control part 60, and a third internal space 61 are formed adjacent to each other to communicate in the stated order.

The buffer space 12, the first internal space 20, the second internal space 40, and the third internal space 61 are spaces (regions) inside the sensor element 101 looking as if they were provided by hollowing out the spacer layer 5, and having an upper portion, a lower portion, and a side portion respectively defined by the lower surface of the second solid electrolyte layer 6, the upper surface of the first solid electrolyte layer 4, and a side surface of the spacer layer 5. The gas inlet 10 may similarly look as if it was provided by hollowing out the spacer layer 5 in the first leading end portion 101a separately from the first diffusion control part 11. In this case, the first diffusion control part 11 is formed inside and adjacent to the gas inlet 10.

The first diffusion control part 11, the second diffusion control part 13, the third diffusion control part 30, and the fourth diffusion control part 60 are each provided as two horizontally long slits (whose openings have longitudinal directions perpendicular to the page of FIG. 2). A part extending from the gas inlet 10 to the third internal space 61 as the farthest internal space is also referred to as a gas distribution part.

On a side of the second leading end portion 101b of the sensor element 101, a reference gas introduction space 43 having a side portion defined by a side surface of the first solid electrolyte layer 4 is provided between an upper surface of the third substrate layer 3 and a lower surface of the spacer layer 5. The reference gas introduction space 43 opens to the reference gas space SP in the outer tube 104, and air as the reference gas is introduced from the reference gas space SP into the reference gas introduction space 43.

An air introduction layer 48 is a layer formed of porous alumina, and the reference gas is introduced into the air introduction layer 48 through the reference gas introduction space 43. The air introduction layer 48 is formed to cover a reference electrode 42.

The reference electrode 42 is an electrode formed to be sandwiched between the upper surface of the third substrate layer 3 and the first solid electrolyte layer 4, and the air introduction layer 48 leading to the reference gas introduction space 43 is provided around the reference electrode 42 as described above. As will be described below, an oxygen concentration (oxygen partial pressure) in the first internal space 20 and the second internal space 40 can be measured using the reference electrode 42.

In the gas distribution part, the gas inlet 10 (first diffusion control part 11) is a part opening to an external space, and the measurement gas is taken from the external space into the sensor element 101 through the gas inlet 10.

The first diffusion control part 11 is a part providing predetermined diffusion resistance to the taken measurement gas.

The buffer space 12 is a space provided to guide the measurement gas introduced through the first diffusion control part 11 to the second diffusion control part 13.

The second diffusion control part 13 is a part providing predetermined diffusion resistance to the measurement gas introduced from the buffer space 12 into the first internal space 20.

In introducing the measurement gas from outside the sensor element 101 into the first internal space 20, the measurement gas having abruptly been taken into the sensor element 101 through the gas inlet 10 due to pressure fluctuations (pulsation of exhaust pressure in a case where the measurement gas is the exhaust gas of the vehicle) of the measurement gas in the external space is not directly introduced into the first internal space 20 but is introduced into the first internal space 20 after concentration fluctuations of the measurement gas are canceled through the first diffusion control part 11, the buffer space 12, and the second diffusion control part 13. This makes the concentration fluctuations of the measurement gas introduced into the first internal space 20 almost negligible.

The first internal space 20 is provided as a space to adjust oxygen partial pressure of the measurement gas introduced through the second diffusion control part 13. The oxygen partial pressure is adjusted by operation of a main pump cell 21.

The main pump cell 21 is an electrochemical pump cell including an inner pump electrode (also referred to as a main pump electrode) 22, an outer (out-of-space) pump electrode 23, and the second solid electrolyte layer 6 sandwiched between these electrodes. The inner pump electrode 22 has a ceiling electrode portion 22a provided on substantially the entire lower surface of a portion of the second solid electrolyte layer 6 facing the first internal space 20, and the outer pump electrode 23 is provided in a region, on an upper surface of the second solid electrolyte layer 6 (one main surface of the sensor element 101), corresponding to the ceiling electrode portion 22a to be exposed to the external space.

The inner pump electrode 22 is formed on upper and lower solid electrolyte layers (the second solid electrolyte layer 6 and the first solid electrolyte layer 4) defining the first internal space 20. Specifically, the ceiling electrode portion 22a is formed on the lower surface of the second solid electrolyte layer 6, which provides a ceiling surface to the first internal space 20, and a bottom electrode portion 22b is formed on the upper surface of the first solid electrolyte layer 4, which provides a bottom surface to the first internal space 20. The ceiling electrode portion 22a and the bottom electrode portion 22b are connected by a conducting portion (not illustrated) provided on a side wall surface (an inner surface) of the spacer layer 5 forming opposite side wall portions of the first internal space 20.

The ceiling electrode portion 22a and the bottom electrode portion 22b are provided to be rectangular in plan view. Only the ceiling electrode portion 22a or only the bottom electrode portion 22b may be provided.

The inner pump electrode 22 and the outer pump electrode 23 are each formed as a porous cermet electrode. In particular, the inner pump electrode 22 to be in contact with the measurement gas is formed using a material having a weakened reducing ability with respect to a NOx component in the measurement gas. For example, the inner pump electrode 22 is formed as a cermet electrode of an Au—Pt alloy containing Au of approximately 0.6 wt % to 1.4 wt % and $ZrO_2$ to have a porosity of 5% to 40% and a thickness of 5 μm to 20 μm. A weight ratio $Pt:ZrO_2$ of the Au—Pt alloy and $ZrO_2$ is only required to be approximately 7.0:3.0 to 5.0:5.0.

On the other hand, the outer pump electrode 23 is formed, for example, as a cermet electrode of Pt or an alloy thereof and $ZrO_2$ to be rectangular in plan view.

The main pump cell 21 can pump out oxygen in the first internal space 20 to the external space or pump in oxygen in the external space to the first internal space 20 by applying a desired pump voltage Vp0 across the inner pump electrode 22 and the outer pump electrode 23 from a variable power supply 24, under control performed by the element operation control part 1101, to allow a main pump current Ip0 to flow between the inner pump electrode 22 and the outer pump electrode 23 in a positive or negative direction. The pump voltage Vp0 applied across the inner pump electrode 22 and the outer pump electrode 23 in the main pump cell 21 is also referred to as a main pump voltage Vp0.

To detect the oxygen concentration (oxygen partial pressure) in an atmosphere in the first internal space 20, the inner pump electrode 22, the second solid electrolyte layer 6, the spacer layer 5, the first solid electrolyte layer 4, the third substrate layer 3, and the reference electrode 42 constitute a main sensor cell 80 as an electrochemical sensor cell.

The oxygen concentration (oxygen partial pressure) in the first internal space 20 can be known by measuring electromotive force V0 as a potential difference between the inner pump electrode 22 and the reference electrode 42 in the main sensor cell 80.

Furthermore, the element operation control part 1101 performs feedback control of the main pump voltage Vp0 so that the electromotive force V0 is constant, thereby to control the main pump current Ip0. The oxygen concentration in the first internal space 20 is thereby maintained at a predetermined constant value.

The third diffusion control part 30 is a part providing predetermined diffusion resistance to the measurement gas having an oxygen concentration (oxygen partial pressure) controlled by operation of the main pump cell 21 in the first internal space 20, and guiding the measurement gas to the second internal space 40.

The second internal space 40 is provided as a space to further adjust the oxygen partial pressure of the measurement gas introduced through the third diffusion control part 30. The oxygen partial pressure is adjusted by operation of an auxiliary pump cell 50. The oxygen concentration of the measurement gas is adjusted with higher accuracy in the second internal space 40.

After the oxygen concentration (oxygen partial pressure) is adjusted in advance in the first internal space 20, the auxiliary pump cell 50 further adjusts the oxygen partial pressure of the measurement gas introduced through the third diffusion control part 30 in the second internal space 40.

The auxiliary pump cell 50 is an auxiliary electrochemical pump cell including an auxiliary pump electrode 51, the outer pump electrode 23 (not limited to the outer pump electrode 23 and only required to be any appropriate electrode outside the sensor element 101), and the second solid electrolyte layer 6. The auxiliary pump electrode 51 has a ceiling electrode portion 51a provided on substantially the entire lower surface of a portion of the second solid electrolyte layer 6 facing the second internal space 40.

The auxiliary pump electrode 51 is provided in the second internal space 40 in a similar form to the inner pump electrode 22 provided in the first internal space 20 described previously. That is to say, the ceiling electrode portion 51a is formed on the second solid electrolyte layer 6, which provides a ceiling surface to the second internal space 40, and a bottom electrode portion 51b is formed on the first solid electrolyte layer 4, which provides a bottom surface to the second internal space 40. The ceiling electrode portion 51a and the bottom electrode portion 51b are rectangular in plan view, and are connected by a conducting portion (not illustrated) provided on the side wall surface (inner surface) of the spacer layer 5 forming opposite side wall portions of the second internal space 40.

As with the inner pump electrode 22, the auxiliary pump electrode 51 is formed using a material having a weakened reducing ability with respect to the NOx component in the measurement gas.

The auxiliary pump cell 50 can pump out oxygen in an atmosphere in the second internal space 40 to the external space or pump in oxygen in the external space to the second internal space 40 by applying a desired voltage (an auxiliary pump voltage) Vp1 across the auxiliary pump electrode 51 and the outer pump electrode 23 under control performed by the element operation control part 1101.

To control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an auxiliary sensor cell 81 as an electrochemical sensor cell. In the auxiliary sensor cell 81, electromotive force V1 as a potential difference caused between the auxiliary pump electrode 51 and the reference electrode 42 in accordance with the oxygen partial pressure in the second internal space 40 is detected.

The auxiliary pump cell 50 performs pumping using a variable power supply 52 whose voltage is controlled based on the electromotive force V1 detected in the auxiliary sensor cell 81. The oxygen partial pressure in the atmosphere in the second internal space 40 is thereby feedback controlled to a low partial pressure having substantially no effect on measurement of NOx.

At the same time, a resulting auxiliary pump current Ip1 is used to control the electromotive force in the main sensor cell 80. Specifically, the auxiliary pump current Ip1 is input, as a control signal, into the main sensor cell 80, and, through control of the electromotive force V0 therein, the oxygen partial pressure of the measurement gas introduced through the third diffusion control part 30 into the second internal space 40 is controlled to have a gradient that is always constant. In use as the NOx sensor, the oxygen concentration in the second internal space 40 is maintained at a constant value of approximately 0.001 ppm by the action of the main pump cell 21 and the auxiliary pump cell 50.

The fourth diffusion control part 60 is a part providing predetermined diffusion resistance to the measurement gas having an oxygen concentration (oxygen partial pressure) controlled by operation of the auxiliary pump cell 50 in the second internal space 40, and guiding the measurement gas to the third internal space 61.

The third internal space 61 is provided as a space (measurement internal space) to perform processing concerning measurement of the nitrogen oxide (NOx) concentration of the measurement gas introduced through the fourth diffusion control part 60. The NOx concentration is measured by operation of a measurement pump cell 41 in the third internal space 61. The measurement gas having the oxygen concentration adjusted with high accuracy in the second internal space 40 is introduced into the third internal space 61, so that the NOx concentration can be measured with high accuracy in the gas sensor 100.

The measurement pump cell 41 is to measure the NOx concentration of the measurement gas introduced into the third internal space 61. The measurement pump cell 41 is an electrochemical pump cell including a measurement electrode 44, the outer pump electrode 23, the second solid electrolyte layer 6, the spacer layer 5, and the first solid electrolyte layer 4. The measurement electrode 44 is provided on an upper surface of a portion of the first solid electrolyte layer 4 facing the third internal space 61 to be separated from the third diffusion control part 30.

The measurement electrode 44 is a porous cermet electrode of a noble metal and a solid electrolyte. For example, the measurement electrode 44 is formed as a cermet electrode of Pt or an alloy of Pt and another noble metal, such as Rh, and $ZrO_2$ as a constituent material for the sensor element 101. The measurement electrode 44 also functions as a NOx reduction catalyst to reduce NOx present in an atmosphere in the third internal space 61.

The measurement pump cell 41 can pump out oxygen generated through decomposition of NOx in the atmosphere in the third internal space 61, and detect the amount of generated oxygen as a pump current Ip2 under control performed by the element operation control part 1101.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute a measurement sensor cell 82 as an electrochemical sensor cell. A variable power supply 46 is feedback controlled based on electromotive force V2 as a potential difference caused between the measurement electrode 44 and the reference electrode 42 detected by the measurement sensor cell 82 in accordance with the oxygen partial pressure in the third internal space 61.

NOx in the measurement gas introduced into the third internal space 61 is reduced by the measurement electrode 44 ($2NO \rightarrow N_2 + O_2$) to generate oxygen. Oxygen as generated is to be pumped by the measurement pump cell 41, and, in this case, a voltage (measurement pump voltage) Vp2 of the variable power supply 46 is controlled so that the electromotive force V2 detected by the measurement sensor cell 82 is constant. The amount of oxygen generated around the measurement electrode 44 is proportional to the NOx concentration of the measurement gas, and thus the NOx concentration of the measurement gas is to be calculated using the pump current Ip2 in the measurement pump cell 41. The pump current Ip2 is hereinafter also referred to as a NOx current Ip2 or a measurement pump current Ip2.

In the case that the measurement electrode 44, the first solid electrolyte layer 4, the third substrate layer 3, and the reference electrode 42 are combined to constitute an oxygen partial pressure detection means as an electrochemical sensor cell, electromotive force in accordance with a difference between the amount of oxygen generated through reduction of a NOx component in the atmosphere around the measurement electrode 44 and the amount of oxygen contained in reference air can be detected, and the concentration of the NOx component in the measurement gas can thereby be determined.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure of the measurement gas outside the sensor can be detected using electromotive force Vref determined by the sensor cell 83.

In FIG. 2, wiring for electrically connecting electrodes forming various pump cells and sensor cells to each part outside the sensor element 101 is schematically shown for ease of illustration. Electrode leads connecting electrodes of the pump cells and the sensor cells to the terminal electrodes, however, are arranged in or on a side of the actual sensor element 101.

Figure 4:
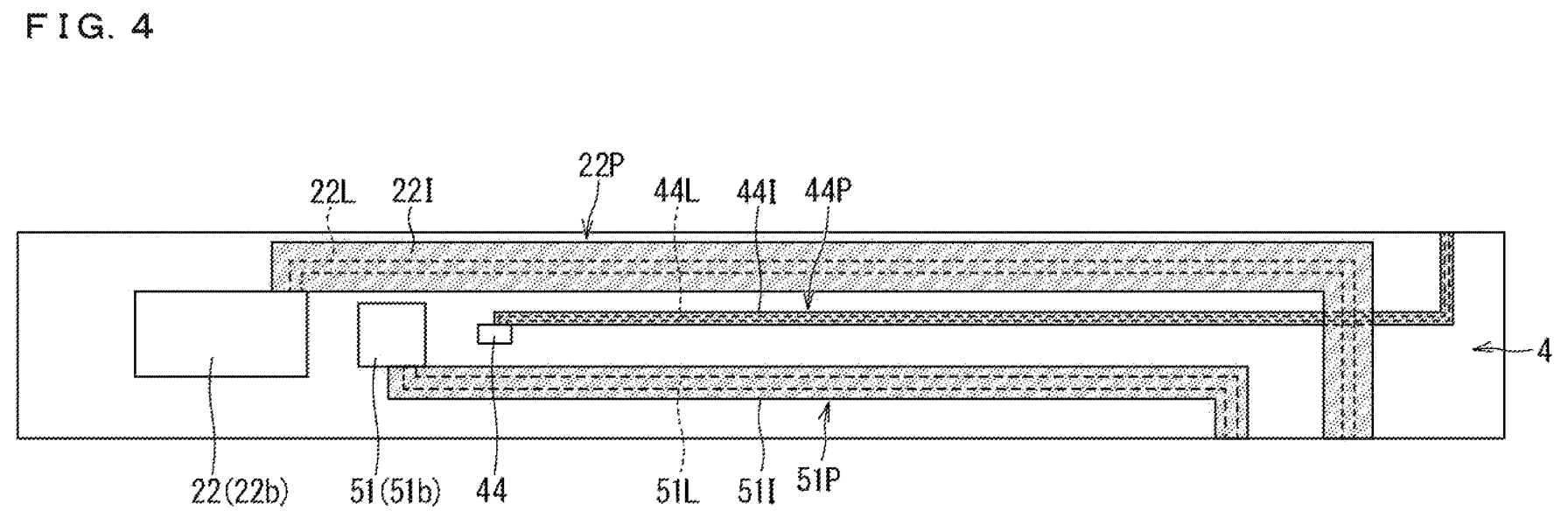
Figure 5:
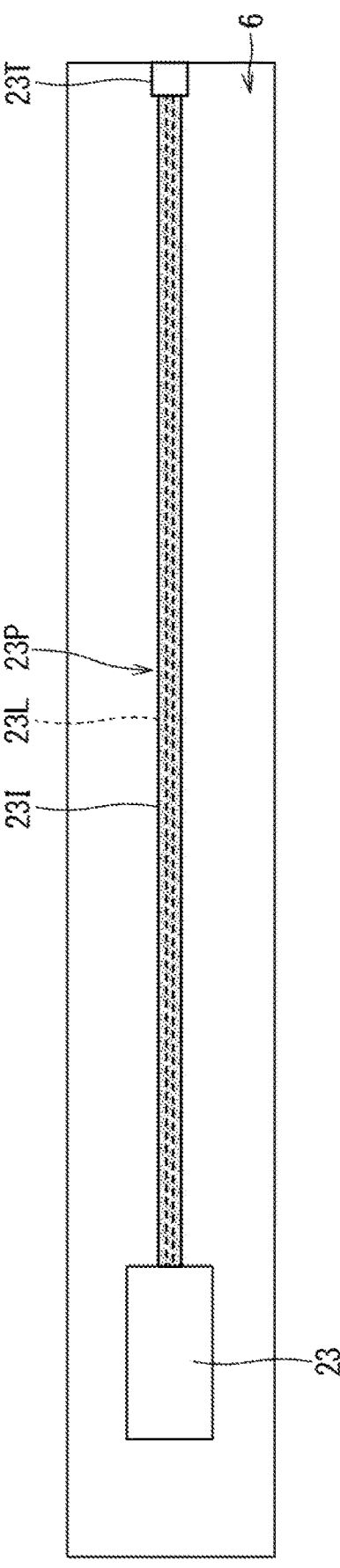
FIG. 5 is a plan view illustrating the layout of an electrode lead portion including an electrode lead extending from an outer pump electrode 23.

FIG. 4 is a plan view illustrating the layout of electrode lead portions including electrode leads extending from the main pump electrode 22 (more particularly the bottom electrode portion 22*b*), the auxiliary pump electrode 51 (more particularly the bottom electrode portion 51*b*), and the measurement electrode 44 as one example. FIG. 5 is a plan view illustrating the layout of an electrode lead portion including an electrode lead extending from the outer pump electrode 23.

The bottom electrode portion 22*b*, the bottom electrode portion 51*b*, and the measurement electrode 44 are arranged on the first solid electrolyte layer 4. A main pump electrode lead 22L surrounded by a main pump electrode lead insulating layer 221 extends from the bottom electrode portion 22*b*, an auxiliary pump electrode lead 51L surrounded by an auxiliary pump electrode lead insulating layer 51I extends from the bottom electrode portion 51*b*, and a measurement electrode lead 44L surrounded by a measurement electrode lead insulating layer 44I extends from the measurement electrode 44 toward the second leading end portion 101*b*. On the other hand, the outer pump electrode 23 is disposed on the second solid electrolyte layer 6. An outer pump electrode lead 23L surrounded by an outer pump electrode lead insulating layer 23I extends from the outer pump electrode 23 toward the second leading end portion 101*b*. The insulating layers provide insulation between the electrode leads and the solid electrolyte forming the sensor element 101.

A region including the main pump electrode lead 22L and the main pump electrode lead insulating layer 22I and surrounded by the solid electrolyte (mainly the first solid electrolyte layer 4 and the spacer layer 5) is hereinafter generically referred to as a main pump electrode lead portion 22P. A region including the auxiliary pump electrode lead 51L and the auxiliary pump electrode lead insulating layer 51I and surrounded by the solid electrolyte (mainly the first solid electrolyte layer 4 and the spacer layer 5) is hereinafter similarly generically referred to as an auxiliary pump electrode lead portion 51P. Furthermore, a region including the measurement electrode lead 44L and the measurement electrode lead insulating layer 44I and surrounded by the solid electrolyte (mainly the first solid electrolyte layer 4 and the spacer layer 5) is hereinafter generically referred to as a measurement electrode lead portion 44P.

The outer pump electrode lead 23L is connected to a terminal electrode 23T located in the second leading end portion 101*b*. While the outer pump electrode lead insulating layer 231 is disposed straight (linearly) along the outer pump electrode lead 23L in FIG. 5, the outer pump electrode lead insulating layer 231 may be disposed to be planar (laminar) between the outer pump electrode 23 and the terminal electrode 23T.

On the other hand, the main pump electrode lead 22L, the auxiliary pump electrode lead 51L, and the measurement electrode lead 44L are each interlayer wiring having a large portion being buried between the first solid electrolyte layer 4 and the spacer layer 5, but are bent to sides of the element in the vicinity of the second leading end portion 101*b*. Furthermore, although not illustrated, the main pump electrode lead 22L, the auxiliary pump electrode lead 51L, and the measurement electrode lead 44L are connected to an upper or a lower portion in the thickness direction via through holes in the vicinity of side end portions of the element while being respectively surrounded by the main pump electrode lead insulating layer 221, the auxiliary pump electrode lead insulating layer 51I, and the measurement electrode lead insulating layer 44I, and are each connected to any of a plurality of unillustrated terminal electrodes similar to the terminal electrode 23T located in the second leading end portion 101*b* by the other interlayer wiring. In the present embodiment, a state of surrounding the electrode leads by the lead insulating layers includes a state of covering the electrode leads with the lead insulating layers and a state of sandwiching the electrode leads by the lead insulating layers.

The main pump electrode lead 22L, the auxiliary pump electrode lead 51L, the measurement electrode lead 44L, and the outer pump electrode lead 23L are preferably formed of platinum. The main pump electrode lead insulating layer 221, the auxiliary pump electrode lead insulating layer 51I, the measurement electrode lead insulating layer 44I, and the outer pump electrode lead insulating layer 231 are preferably formed of alumina.

The sensor element 101 further includes a heater part 70 playing a role in temperature adjustment of heating the sensor element 101 and maintaining the temperature thereof to enhance oxygen ion conductivity of the solid electrolyte forming the base part.

The heater part 70 mainly includes a heater electrode 71, a heater element 72, a heater lead 72*a*, a through hole 73, a heater insulating layer 74, a pressure dissipation hole 75, and a heater resistance detection lead, which is not illustrated in FIG. 2. A portion of the heater part 70 other than the heater electrode 71 is buried in the base part of the sensor element 101.

The heater electrode 71 is an electrode formed to be in contact with a lower surface of the first substrate layer 1 (the other main surface of the sensor element 101).

The heater element 72 is a resistive heating element provided between the second substrate layer 2 and the third substrate layer 3. The heater element 72 generates heat by being powered from a heater power supply, which is not illustrated in FIG. 2, outside the sensor element 101 through the heater electrode 71, the through hole 73, and the heater lead 72*a*, which constitute a current-carrying path. The heater element 72 is formed of Pt, or contains Pt as a main component. The heater element 72 is buried, in a predetermined range of the sensor element 101 in which the gas distribution part is provided, to oppose the gas distribution part in the thickness direction of the element. The heater element 72 is provided to have a thickness of approximately 10 μm to 30 μm.

In the sensor element 101, each part of the sensor element 101 can be heated to a predetermined temperature and the temperature can be maintained by allowing a current to flow through the heater electrode 71 to the heater element 72, under control performed by the element operation control part 1101, to thereby cause the heater element 72 to generate heat. Specifically, the sensor element 101 is heated so that the temperature of the solid electrolyte and the electrodes in the vicinity of the gas distribution part is approximately 700° C. to 900° C. The oxygen ion conductivity of the solid electrolyte forming the base part of the sensor element 101 is enhanced by the heating. A heating temperature of the heater element 72 when the gas sensor 100 is in use (when the sensor element 101 is driven) is referred to as a sensor element driving temperature.

A degree of heat generation (heater temperature) of the heater element 72 is grasped by a magnitude of a resistance value (heater resistance) of the heater element 72.

Although not illustrated in FIG. 2, an electrode protective layer covering the outer pump electrode 23 may be provided on a side of the one main surface of the sensor element 101 to protect the outer pump electrode 23.

When the gas sensor 100 having a configuration as described above measures the NOx concentration, the element operation control part 1101 operates the main pump cell 21 and, further, the auxiliary pump cell 50 so that feedback control to make the oxygen concentration in the first internal space 20 and, further, the second internal space 40 constant is performed, and the measurement gas having a constant oxygen concentration is introduced into the third internal space 61, and reaches the measurement electrode 44. For example, when the measurement gas is a lean atmosphere, the measurement gas having oxygen partial pressure sufficiently reduced to a degree (e.g., 0.0001 ppm to 1 ppm) having substantially no effect on measurement of NOx is introduced into the third internal space 61.

The measurement electrode 44 reduces NOx in the reaching measurement gas to generate oxygen. While the oxygen is pumped out by the measurement pump cell 41, the NOx current Ip2 flowing at the pumping out has a constant functional relationship (hereinafter referred to as sensitivity characteristics) with the NOx concentration of the measurement gas.

The sensitivity characteristics are identified in advance prior to practical use of the gas sensor 100 using a plurality of types of model gases having known NOx concentrations, and data thereof is stored in the NOx concentration identification part 1102 (more particularly the memory). In practical use of the gas sensor 100, a signal representing a value of the NOx current Ip2 flowing in accordance with the NOx concentration of the measurement gas is provided to the NOx concentration identification part 1102 on a moment-to-moment basis. The NOx concentration identification part 1102 successively calculates NOx concentrations based on the value and the identified sensitivity characteristics, and outputs values thereof as NOx sensor detection values. The NOx concentration of the measurement gas can thereby be grasped in almost real time using the gas sensor 100.

<Generation of Contaminated Gas in Reference Gas Space>

In a case of a gas sensor having a configuration in which the outer tube 104 and the rubber plug 106 surround the reference gas space SP as with the gas sensor 100 according to the present embodiment, and used in a high temperature environment, a contaminated gas might be generated in the reference gas space SP due to volatilization of an oil content adhering to an inner surface 104a of the outer tube 104 and generation of a gas from the rubber plug 106, and, as a result, the NOx current Ip2 might change. The contaminated gas is more likely to be generated particularly under a higher temperature gas condition and a harsher environment in which heat is accumulated around the main body.

Figure 6:
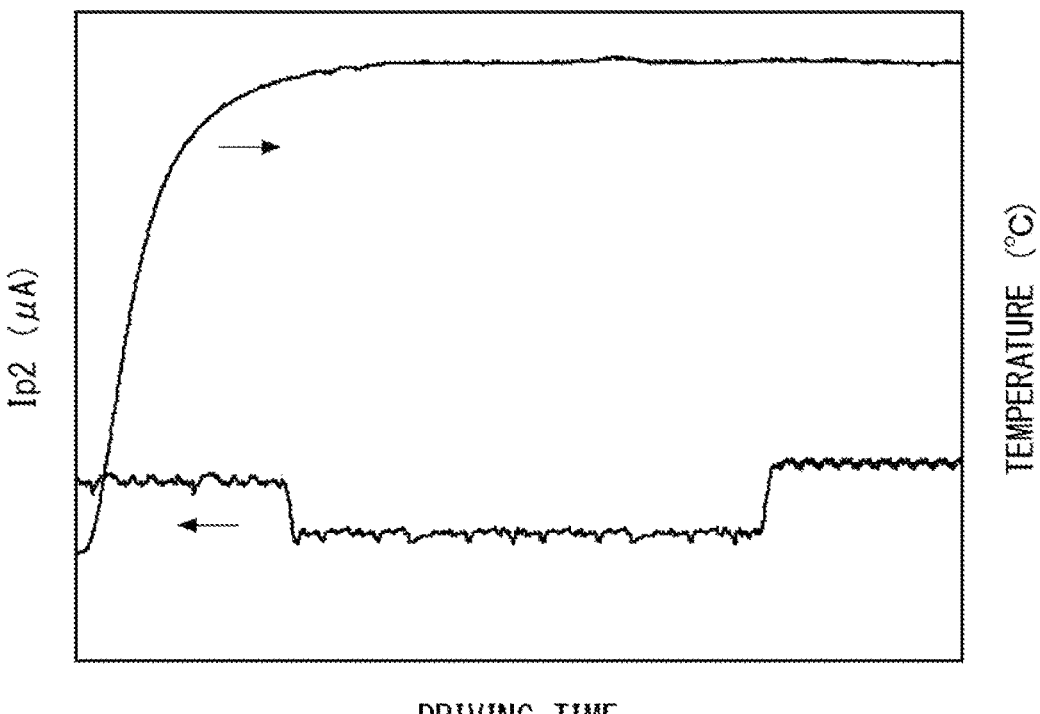
FIG. 6 is one example of a graph showing a change in NOx current Ip2 from start of operation along with a change in temperature of a rubber plug 106 when the gas sensor is operated under a model gas atmosphere having a constant NOx concentration.

FIG. 6 is one example of a graph showing a change in NOx current Ip2 from the start of operation along with a change in temperature of the rubber plug 106 when such a gas sensor is operated under a model gas atmosphere having a constant NOx concentration. In FIG. 6, the NOx current Ip2 to be kept constant temporarily decreases after an increase in temperature of the rubber plug 106. Then, when and after the temperature of the rubber plug 106 is stabilized, the NOx current Ip2 increases to the same degree as an initial peak value, and becomes substantially constant.

The temporary decrease in NOx current in FIG. 6 is believed to be due to ingress of a contaminated gas as described above generated in a process of heating the gas sensor into the third internal space 61 in which the measurement electrode 44 is disposed through the measurement electrode lead portion described below. The increase in value of the NOx current Ip2 after an elapse of a certain time period is believed to be due to emission of all the contaminated gas as a result of sufficient heating of the outer tube 104 and the rubber plug 106.

Such fluctuations of the NOx current Ip2 naturally become a factor for reduction in measurement accuracy of the NOx concentration of the gas sensor, even temporarily. The contaminated gas is not always generated only after the start of use as shown in FIG. 6.

<Correlation Between Ip2 Offset and Amount of Output Fluctuations>

In the gas sensor 100 according to the present embodiment, the correction processing part 1103 corrects the NOx current Ip2 fluctuating due to generation of the contaminated gas as described above to secure measurement accuracy of the NOx concentration. An Ip2 offset is used for correction.

The Ip2 offset is herein a magnitude (an offset current value) of the pump current Ip2 flowing through the measurement pump cell 41 when the measurement gas does not contain NOx. As described above, the pump current Ip2 flows when the measurement pump cell 41 pumps out oxygen generated by the measurement electrode 44 decomposing NOx contained in the measurement gas containing little oxygen reaching the third internal space 61. The pump current Ip2 thus originally does not flow when the measurement gas does not contain NOx. The pump current Ip2, however, actually flows due to pumping out of trace amounts of oxygen remaining in the measurement gas and oxygen entering into the third internal space 61 through the measurement electrode lead portion 44P even when the measurement gas does not contain NOx. A magnitude of the pump current Ip2 in such a case is particularly referred to as the Ip2 offset.

A large amount of the contaminated gas entering into the third internal space 61 through the measurement electrode lead portion 44P in the gas sensor 100 means that the gas sensor 100 has a configuration in which a gas is likely to enter (flow) from the reference gas space SP into the third internal space 61 through the measurement electrode lead portion 44P. Therefore, in the gas sensor 100 having such a configuration, fluctuations of the NOx current Ip2 increase when the contaminated gas is generated, and the Ip2 offset at a time when the measurement gas does not contain NOx also increases. That is to say, there is a positive correlation between the Ip2 offset and the amount of output fluctuations of the NOx current Ip2.

Figure 7:
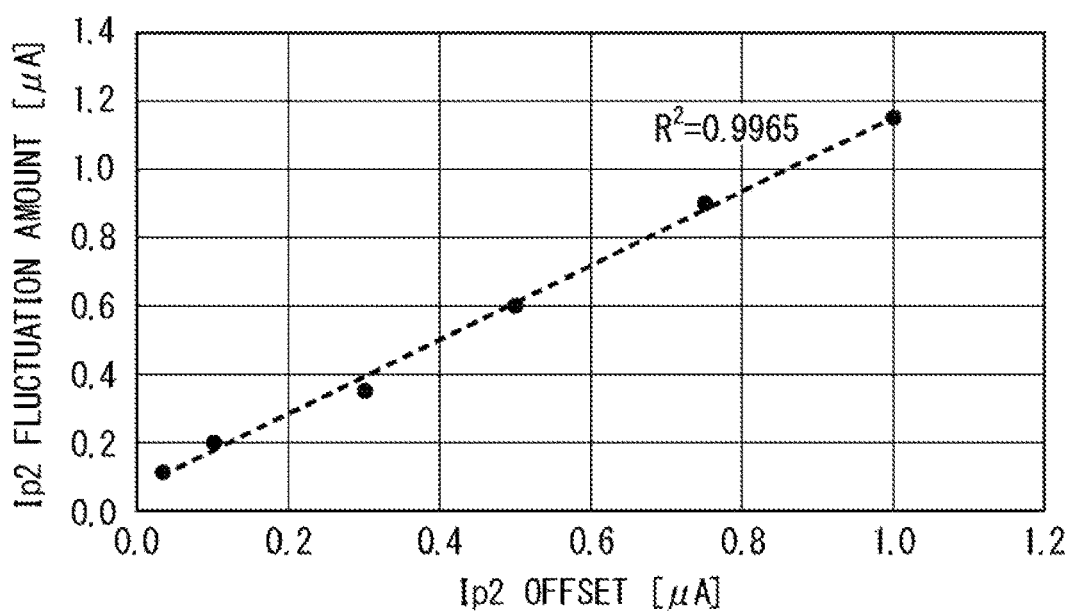
FIG. 7 shows one example of a correlation between an Ip2 offset and an amount of output fluctuations of the NOx current Ip2.

FIG. 7 shows one example of the correlation between the Ip2 offset and the amount of output fluctuations of the NOx current Ip2. FIG. 7 is a graph obtained by evaluating the Ip2 offset and the amount of output fluctuations of the NOx current Ip2 for each of six different gas sensors 100, and plotting the Ip2 offset on a horizontal axis against the amount of output fluctuations of the NOx current Ip2 (shown as "Ip2 FLUCTUATION AMOUNT" in FIG. 7) on a vertical axis. It can be seen from FIG. 7 that there is a strong positive correlation between the Ip2 offset and the amount of output fluctuations of the NOx current Ip2. A determination coefficient R2 as the square of a correlation coefficient R was 0.9965.

A value of the Ip2 offset was evaluated by using, as the measurement gas, a model gas containing neither oxygen nor NOx($O_2$=0%, NO=0%, $H_2O$=3%, and the balance is $N_2$).

On the other hand, the amount of output fluctuations of the NOx current Ip2 was generally determined by obtaining a profile of the NOx current Ip2 as shown in FIG. 6.

Figure 8:
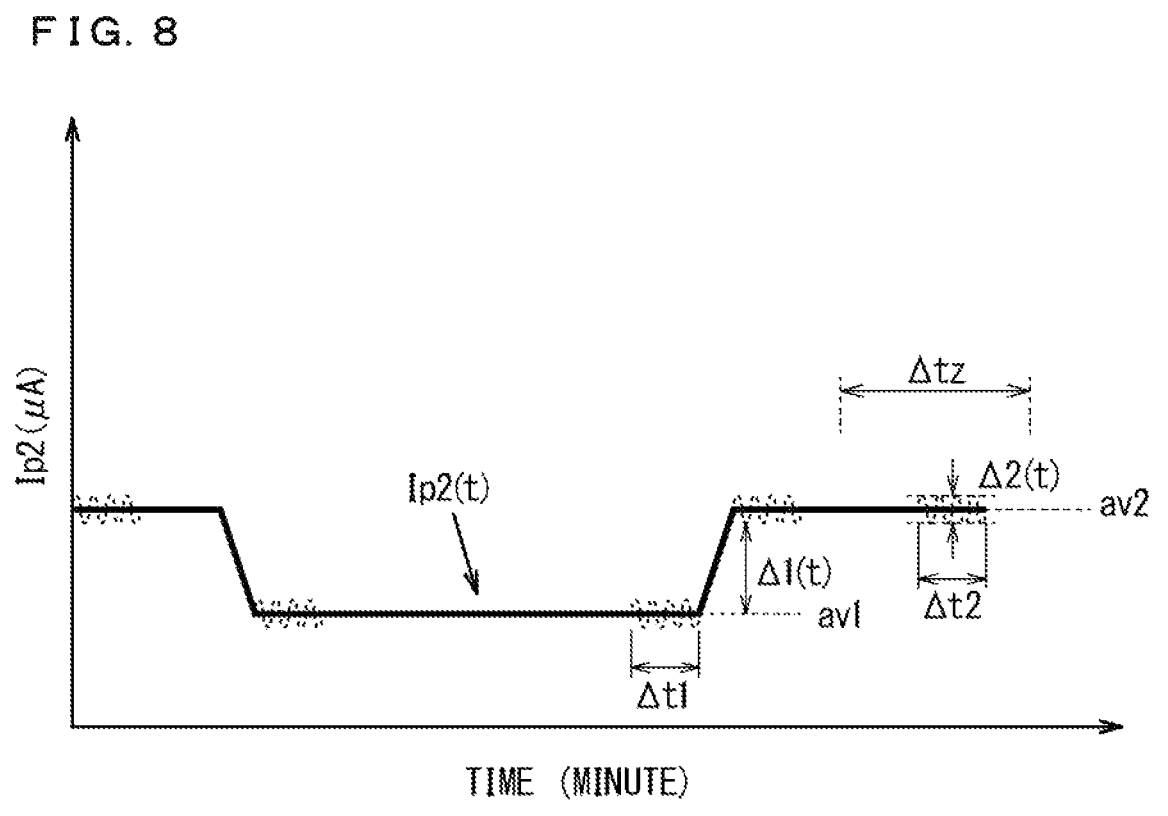

FIG. 8 describes how to evaluate the amount of output fluctuations. Specifically, a profile Ip2($t$) corresponding to a function of the NOx current Ip2 to time as shown in FIG. 8 was obtained by starting each of the gas sensors under a model gas atmosphere having a temperature of 1050° C., an air ratio λ of 1.05, and a NOx concentration of 100 ppm, and continuously measuring the NOx current Ip2 while controlling heating of the heater part 70 so that a temperature of the rubber plug 106 is eventually maintained at a constant temperature of 300° C.

The profile Ip2($t$) similar to that in the example shown in FIG. 6 was obtained for each of the gas sensors although it varies to a greater or lesser degree. That is to say, the NOx current Ip2 became substantially constant shortly after the start of operation of the gas sensor, but decreased once to become substantially constant due to generation of the contaminated gas, and then increased again after a while to eventually become substantially constant at substantially the same value as that at the start of operation.

While the profile Ip2($t$) is shown in a solid polygonal line in FIG. 8 for ease of understanding, the profile Ip2($t$) actually had some fluctuations as schematically shown in broken lines.

In evaluating the amount of output fluctuations targeted for the profile Ip2($t$) as described above, an average value av1 of values of the NOx current Ip2 during a predetermined time period Δt1 (e.g., 10 minutes) immediately before the increase from a substantially constant state after the decrease was identified first. The reason the average value was taken is because a value appearing to be substantially constant actually fluctuated.

Next, a difference value Δ1($t$) of the value of the NOx current Ip2 when and after the NOx current Ip2 became a substantially constant state after the increase from the average value av1 and a difference value Δ2($t$) between a maximum value and a minimum value of the NOx current Ip2 in the substantially constant state after the increase were determined. The difference value Δ1($t$) and the difference value Δ2($t$) are dynamic values fluctuating in accordance with fluctuations of the value of the NOx current Ip2 after the increase, and thus are expressed as functions of time.

Then, it was determined that fluctuations due to the contaminated gas were eliminated, and the NOx current Ip2 became substantially constant at an original value when a predetermined observation time period Δtz (e.g., 60 minutes) has elapsed since the difference value Δ1($t$) and the difference value Δ2($t$) satisfying an inequality (1) shown below.

$$\text{difference value }\Delta\mathbf{1}(t) > 2 \times \text{difference value }\Delta\mathbf{2}(t) \quad (1)$$

Besides, an average value av2 of values of the NOx current Ip2 during a predetermined time period Δt2 (e.g., 10 minutes) immediately before the determination was identified, and a difference value between the average values was calculated as shown below.

$$\text{amount of output fluctuations} = \text{average value av}\mathbf{2} - \text{average value av}\mathbf{1} \quad (2)$$

<Correction of NOx Concentration>

In the present embodiment, the correction processing part 1103 corrects the NOx concentration fluctuating due to generation of the contaminated gas in the reference gas space SP at the start of operation of the gas sensor 100 using the correlation between the amount of output fluctuations of the NOx current Ip2 and the Ip2 offset as shown in FIG. 7. That is to say, while the Ip2 offset is a value unique to each of the gas sensors 100, the correlation between the amount of output fluctuations of the NOx current Ip2 and the Ip2 offset is a general relationship satisfied by many gas sensors 100, so that, when each of the gas sensors 100 is in use, the NOx concentration can be corrected by applying an offset value of the gas sensor 100 to the correlation identified in advance.

In a case of industrially mass-produced gas sensors 100, some of many manufactured gas sensors 100 are sampled to determine the amount of output fluctuations of the NOx current Ip2 and the Ip2 offset, and the correlation as shown in FIG. 7 is identified from the determined values. The identified correlation is stored in the correction processing part 1103 (more particularly the memory) as correction mapping information. On the other hand, the Ip2 offset is also identified for each of the gas sensors 100 when the above-mentioned sensitivity characteristics are identified immediately after the manufacture, and is stored in the NOx concentration identification part 1102 as a portion of the sensitivity characteristics. The correction processing part 1103 applies the Ip2 offset acquired from the NOx concentration identification part 1102 to the correlation stored in advance at a time when the correction processing is to be performed to identify the amount of output fluctuations of the NOx current Ip2, and corrects the NOx concentration based on the identified amount of output fluctuations.

Figure 9:
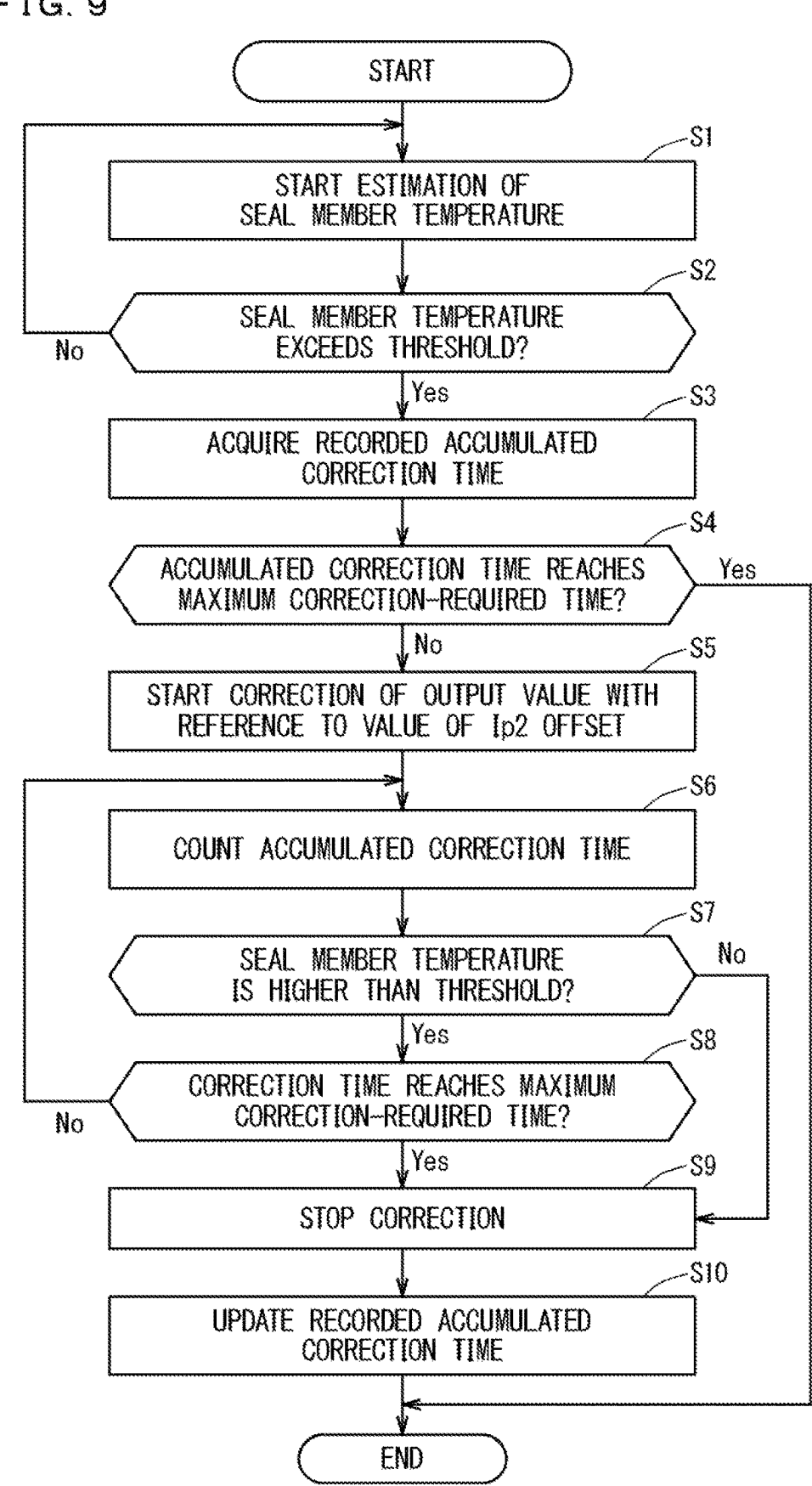
FIG. 9 shows specific procedures for correction processing performed by a correction processing part 1103.

FIG. 9 shows specific procedures for the correction processing performed by the correction processing part 1103.

First, at activation of the gas sensor 100, the seal member temperature estimation part 1103A starts estimation of the temperature (a seal member temperature) of the rubber plug 106 (step S1). The gas sensor 100 is typically activated simultaneously with startup of the vehicle.

The seal member temperature changes depending on an external factor, such as a temperature of the exhaust gas from the engine as the measurement gas, a temperature around the main body of the gas sensor 100, and a flow velocity around the main body changing in accordance with a speed of travel of the vehicle. In the present embodiment, in view of this, a relationship between an actual seal member temperature and a characteristic value (a seal member temperature estimation factor) having an effect on the seal member temperature during travel of the vehicle (i.e., during operation of the gas sensor 100), such as an exhaust gas temperature, the travel speed, and torque is experimentally identified in advance, and the identified relationship is stored in the seal member temperature estimation part 1103A of the correction processing part 1103 as mapping information (seal member temperature estimation information) for estimating the seal member temperature. The seal member temperature estimation part 1103A starts acquisition of an actual value of the seal member temperature estimation factor at activation of the gas sensor 100, and sequentially and continuously compares the actual value and the seal member temperature estimation information to estimate the seal member temperature in almost real time. Note that the outer tube 104 is estimated to be at a higher temperature than the rubber plug 106 when the gas sensor 100 is in use as it is formed of metal and thus has a higher thermal conductivity than the rubber plug 106.

The seal member temperature estimation part 1103A determines whether the estimated seal member temperature exceeds a predetermined threshold temperature (correction performance threshold temperature) set in advance (step S2). The correction performance threshold temperature is herein a minimum temperature to be determined that the NOx concentration is required to be corrected with an increase in temperature of the rubber plug 106 and, further, the outer tube 104 and is identified in advance. In a case where the NOx current Ip2 changes over time as shown in FIG. 6, for example, a temperature when the NOx current Ip2 having once increased decreases from a peak value only by a predetermined value is set to the correction performance threshold temperature.

As long as the seal member temperature estimation part 1103A determines that the seal member temperature does not exceed the correction performance threshold temperature (NO in step S2), only estimation of the seal member temperature is continued. This is because it is believed that the contaminated gas is not generated when the seal member temperature is in a temperature range lower than the correction performance threshold temperature, and the NOx concentration is not required to be corrected. The seal member temperature estimation part 1103A continues estimation of the seal member temperature until the correction processing is stopped.

On the other hand, when the seal member temperature estimation part 1103A determines that the seal member temperature exceeds the correction performance threshold temperature, the correction time measurement part 1103B acquires the accumulated correction time stored at the time (step S3), and determines whether the accumulated correction time reaches a maximum correction-required time set in advance during the manufacture of the gas sensor 100 and recorded on the correction time measurement part 1103B (more particularly the memory) (step S4).

The accumulated correction time is herein an accumulated value of a time during which correction processing to deal with generation of the contaminated gas is performed immediately before the acquisition. The correction time measurement part 1103B measures the time whenever the correction processing is performed, and stores the accumulated value thereof as the accumulated correction time.

The decrease (fluctuations) of the NOx current Ip2 due to generation of the contaminated gas from the rubber plug 106 and the inner surface 104a of the outer tube 104 is merely a phenomenon caused temporarily at activation of the gas sensor 100 shortly after the start of use, and is no longer caused when and after substances to be a contamination source volatilize and evaporate to disappear. The correction processing is not required to be performed on the gas sensor 100 after such a contamination source disappears as the contaminated gas is not generated even when the temperature is increased each time use (activation) is repeated. Thus, in the present embodiment, a maximum time (the maximum correction-required time) determined to require the correction processing is experimentally identified in advance, and stored in the correction time measurement part 1103B. In other words, the correction processing part 1103 is required to perform correction each time the gas sensor 100 is activated until the maximum correction-required time has elapsed.

When the correction time measurement part 1103B determines that the accumulated correction time already reaches the maximum correction-required time (YES in step S4), the correction processing part 1103 does not perform subsequent processing. This means that correction of the NOx concentration to deal with generation of the contaminated gas is no longer needed as a result of the correction processing having been performed so far.

When the correction time measurement part 1103B determines that the accumulated correction time does not reach the maximum correction-required time (NO in step S4), the correction performance part 1103C starts correction of a value of the NOx concentration identified by the NOx concentration identification part 1102 (step S5). That is to say, the correction performance part 1103C applies the value of the Ip2 offset stored in the NOx concentration identification part 1102 to the mapping information showing the correlation between the amount of output fluctuations of the NOx current Ip2 and the Ip2 offset, thereby to identify the amount of correction of the NOx current Ip2. The amount of correction is applied to the sensitivity characteristics stored in the NOx concentration identification part 1102, and the NOx concentration identified by the NOx concentration identification part 1102 is corrected using the amount of correction thus acquired, so that the value of the NOx concentration identified by the NOx concentration identification part 1102 on a moment-to-moment basis is corrected in almost real time. An effect of the fluctuations of the NOx current Ip2 due to generation of the contaminated gas is thereby suitably eliminated from the value of the NOx concentration output from the gas sensor 100.

At a time when the correction performance part 1103C starts correction of the value of the NOx concentration in this manner, the correction time measurement part 1103B starts a count of a time during which correction is performed (step S6). The seal member temperature estimation part 1103A continuously determines whether the estimated seal member temperature is still higher than the correction performance threshold temperature (step S7).

When the seal member temperature estimation part 1103A determines that the estimated seal member temperature is higher than the correction performance threshold temperature (YES in step S7), the correction time measurement part 1103B determines whether the accumulated correction time increasing due to correction being performed reaches the maximum correction-required time (step S8).

When the seal member temperature becomes equal to or lower than the correction performance threshold temperature after the start of correction (NO in step S7) or the accumulated correction time reaches the maximum correction-required time (YES in step S8), the correction performance part 1103C stops correction of the NOx concentration (step S9) as correction of the NOx concentration is no longer required. In addition, the correction time measurement part 1103B adds a correction time having been counted so far to update the accumulated correction time (step S10). The correction processing performed by the correction processing part 1103 thus ends.

When correction is stopped as a result of the accumulated correction time reaching the maximum correction-required time (YES in step S8), the accumulated correction time after the update matches the maximum correction-required time.

In this case, the NOx concentration is no longer corrected when the gas sensor 100 is activated next.

As described above, according to the present embodiment, fluctuations of the NOx concentration due to generation of the contaminated gas in the reference gas space as a space surrounded by the outer tube and the rubber plug at activation of the gas sensor are corrected based on the correlation identified in advance between the Ip2 offset and the amount of output fluctuations of the NOx current Ip2, thereby to suppress temporary deterioration of measurement accuracy of the NOx concentration.

<Modifications>

While the NOx concentration is corrected based on the correlation between the Ip2 offset and the amount of output fluctuations of the NOx current Ip2 in the above-mentioned embodiment, a correlation between a normalized value obtained by dividing the Ip2 offset by the NOx current Ip2 when a measurement gas having a known NOx concentration (e.g., 500 ppm) flows and the amount of output fluctuations of the NOx current Ip2 may be identified and stored in the correction processing part 1103 as the correction mapping information, and the NOx concentration may be corrected based on the correlation.

The Ip2 offset has a value in accordance with the amount of oxygen still remaining in the measurement gas flowing through the gas inlet 10 and reaching the third internal space 61 while oxygen is pumped out and the amount of oxygen entering from the reference gas space SP into the third internal space 61 through the measurement electrode lead portion 44P. The former depends on diffusion resistance of the gas distribution part extending from the gas inlet 10 to the third internal space 61. The correlation with the amount of output fluctuations of the NOx current Ip2 obtained by using a ratio as described above in place of the Ip2 offset itself thus has a higher correlation coefficient. Use of the correlation for correction of the NOx concentration leads to higher accuracy.

While the invention has been shown and described in detail, the foregoing description is in all aspects illustrative and not restrictive. It is therefore understood that numerous modifications and variations can be devised without departing from the scope of the invention.

What is claimed is:

1. A gas sensor capable of sensing a predetermined gas component in a measurement gas, the gas sensor comprising:

a sensor element including an elongated planar base part formed of an oxygen-ion conductive solid electrolyte, and including a sensing part on a side of one end portion thereof;

a casing in which the sensor element is contained and secured; and a controller controlling operation of the gas sensor, wherein the casing includes:

an outer tube having a reference gas space in which a reference gas is present and into which the other end portion of the sensor element protrudes; and a seal member fit into an end portion of the outer tube to seal the reference gas space, the sensor element includes:

at least one oxygen partial pressure adjustment internal space communicating with an inlet for the measurement gas under predetermined diffusion resistance, the inlet for the measurement gas disposed on the side of the one end portion;

a measurement internal space further communicating with the at least one oxygen partial pressure adjustment internal space;

an out-of-space pump electrode disposed at a location other than the at least one oxygen partial pressure adjustment internal space and the measurement internal space;

a measurement electrode disposed to face the measurement internal space;

a measurement pump cell to which a predetermined pump voltage is applied to allow a measurement pump current to flow between the measurement electrode and the out-of-space pump electrode in accordance with a concentration of the predetermined gas component; and a measurement electrode lead portion including a measurement electrode lead and a measurement lead insulating layer, the measurement electrode lead extending from the measurement electrode to electrically connect an outside of the sensor element and the measurement electrode, the measurement lead insulating layer covering the measurement electrode lead, the controller comprising a processor and a memory storing software, the processor which when executing the software stored in the memory configures the processor to:

identify the concentration of the predetermined gas component based on the measurement pump current;

estimate a temperature of the seal member based on temperature estimation information identified in advance, wherein the processor is configured to start acquisition of an actual value of a seal member temperature estimation factor at activation of the gas sensor, and sequentially and continuously compare the actual value and the seal member temperature estimation information to estimate the seal member temperature in approximately real time; and correct the concentration of the predetermined gas component based on a correlation identified in advance between an offset current value or a normalized value of the offset current value and output fluctuations of the measurement pump current at startup of the gas sensor when it is determined that the temperature of the seal member exceeds a predetermined threshold temperature after the startup of the gas sensor, and wherein the offset current value is a magnitude of the measurement pump current when a measurement gas not containing the predetermined gas component flows.

2. The gas sensor according to claim 1, wherein the processor is further configured to:

measure a time during which the concentration of the predetermined gas component is corrected, and stop correction of the concentration of the predetermined gas component when and after an accumulated value of the time measured by the processor reaches a maximum correction-required time set in advance.

* * * * *